United States Patent [19]

Brauer

[11] 4,419,211
[45] Dec. 6, 1983

[54] GAS ANALYSIS SENSOR FOR MEASURING CONCENTRATION OF GAS CONSTITUENT

[76] Inventor: Lothar Brauer, Busseallee 14, 1000 Berlin 37, Fed. Rep. of Germany

[21] Appl. No.: 354,905

[22] Filed: Mar. 4, 1982

[30] Foreign Application Priority Data

Mar. 5, 1981 [DE] Fed. Rep. of Germany ....... 3109224

[51] Int. Cl.³ ............................................. G01N 27/54
[52] U.S. Cl. ........................................ 204/408; 73/23; 73/708
[58] Field of Search ................... 73/4 R, 23, 708, 765; 204/195 P, 195 R, 408; 324/130, 132, 123 R

[56] References Cited

U.S. PATENT DOCUMENTS 3,663,409 5/1972 Greene .......................... 204/195 P
3,685,346 8/1972 Molloy ................................. 73/23

Primary Examiner—G. L. Kaplan
Attorney, Agent, or Firm—Carothers & Carothers

[57] ABSTRACT

In an instrument with a sensor for gas analysis which, based on the principle underlying its measurement, indicates the partial pressure of the gas constituent to be measured, the indication of the change in the partial pressure of the gas constituent is affected by changes in the atmospheric pressure. Such instruments must be calibrated at mean sea level and adjusted for changes in height at the measuring site.

In order to eliminate the need for adjustment or recalibration, there is included in the instrument a pressure-sensitive module to compensate for the effects of the atmospheric pressure on the sensor. The module compensates the measured value directly or by means of a microprocessor with regard to the prevailing pressure conditions.

3 Claims, 1 Drawing Figure

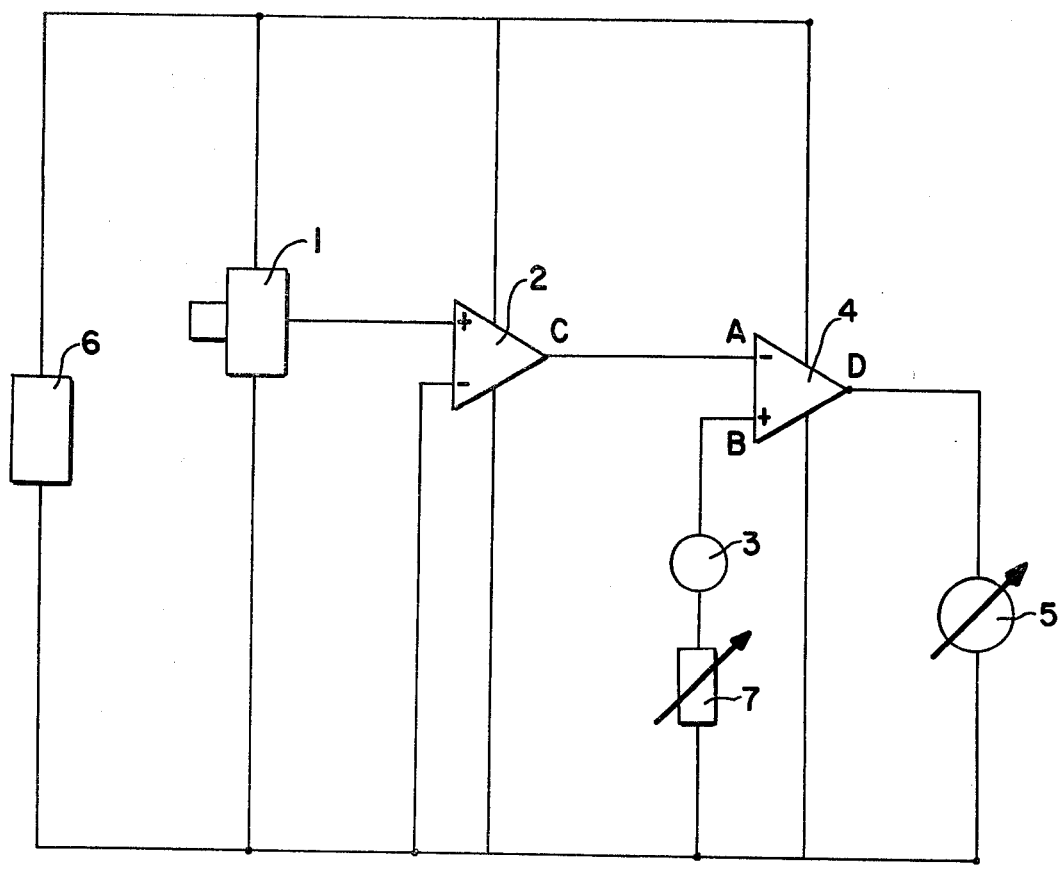

GAS ANALYSIS SENSOR FOR MEASURING CONCENTRATION OF GAS CONSTITUENT

The invention relates to gas analysis sensors for measuring concentration of a gas constituent, and more particularly to electronic equipment utilized in such sensors.

In order to determine the proportions of gas such as, for example, of oxygen, nitrogen oxides, etc., in a gaseous atmosphere to be monitored or of combustible constituents in a fuel-gas atmosphere, use is made, for example, of analyzer cells or sensors which operate on the basis of electro-chemical oxidation. With this measuring procedure, the gaseous constituent to be measured in the gas to be analyzed (test gas) produces in the analyzer cell or in the sensor which, for example, contains two electrodes and an electrolyte, an electro-chemical reaction by means of which there is produced a voltage (EMF) which is proportional to the concentration of the gas to be measured, the said voltage being fed to an indicating device and converted into a concentration indication of the gas to be measured.

With apparatus equipped with analyzer cells or sensors, which operate on the above-mentioned principle, the voltage produced in the sensor is proportional to the concentration or to the partial pressure of the gas in the medium to be analyzed. Should changes take place in the atmospheric pressure, the indicating instrument will follow the change in the partial pressure of the gas, with the consequence that indicating errors must be taken into consideration when making measurements at depths (below sea level) or at high elevations. Until the present, in the event that the elevation was different, an adjustment was made at the measuring site or the indication error was allowed for by a precalibration, or computed and evaluated with the aid of tables. It is obvious that a procedure of this type has its drawbacks and is problematical, especially when measurements have to be made to determine the amounts of gas in a gaseous atmosphere to be monitored below ground.

Consequently, the invention's basic task is to create an electronic measuring device for a sensor whose output is decisively influenced by the partial pressure of the substance to be measured, and to so construct the device that the sensor in independent of external influences, such as all pressure fluctuations, and ensures an automatic matching of the indication to the changing environmental pressure at the measuring site.

This task is accomplished in accordance with the teachings set forth in the appended claims.

The invention is suitable for all sensors such as, for example, those which are also incorporated in infrared gas analyzers and by means of which, in order to determine the concentration of a particular gas constituent in a gaseous atmosphere to be monitored, the current developed in the sensor is proportional to the partial pressure of the gas in the medium being analyzed.

The advantages to be gained with the invention reside, in particular, in the fact that, on using the apparatus at the measuring site, it is unnecessary to carry out any adjustments on the apparatus which allow for changes in the atmospheric pressure, such as adjustments by means of calibrating screws which could subject the apparatus to mechanical stresses of too strong a nature. Dispensing with adjustments of this type constitutes, on the one hand, a simplification in the manipulation of such equipment and, on the other hand, provides a greater reliability and accuracy in the indication, which is especially advantageous when the elevation or the depth of the measuring site is unknown.

An embodiment of the invention will now be described in detail by way of example on the basis of the appended drawing.

The instrument consists essentially of a pressure probe or module 1, a series-connected amplifier 2, a sensor 3 with a series-connected differential amplifier or microprocessor 4 and of an indicating device 5.

A power supply 6 is connected in parallel with the pressure probe or module 1. The pressure detected by the pressure probe 1 is converted into an electric signal which, adjusted via the amplifier 2, is fed to the measurement amplifier 4. The adjustment of the signal is necessary because electric signals of undesired amplitude are emitted by the pressure probe 1 and these values must correspond and be matched to the pressure changes of the partial pressure of the gas in the sensor 3. The input A of the amplifier 4 is connected to the output C of the pressure probe amplifier 2. A change in the value of the input to the input A of the amplifier 4 produces a change in the value of the amplifier's output D and thus a change in the indication in the indicating device 5. With constant pressure relationships, no voltage change takes place via the amplifier branch C, A, D. In the event of changes in the atmospheric pressure such as occur, for example, as the result of increases in pressure at a depth, the sensor gives a higher EMF with the same gas content. This increase in voltage is now compensated by the simultaneous voltage increase at the input A of the amplifier 4, that is, the pressure probe 1 with the series-connected amplifier 2 changes the voltage at the input A of the amplifier 4 by the same amount, corresponding to the higher EMF of the sensor 3. By this means, the difference between the two measuring signals from the pressure probe 1 and from the sensor 3 at the inputs A and B of the amplifier 4 is maintained, so that the output signal D likewise remains unchanged and provides, in the indicating device 5, a true unfalsified measured value which has matched the prevailing pressure relationships.

The normal gas concentration of the gas constituent to be measured is calibrated via the amplifier 4 by means of a potentiometer 7 connected in series with the sensor 3.

I claim:

1. A gas analysis sensor for measuring gas concentration of a gas constituent and including an electronic instrument wherein a voltage is produced from the sensor which is proportional to the concentration of a gas constituent to be measured and said voltage is fed to an indicating device, the improvement comprising said electronic instrument further including:

a pressure-sensitive module adapted to be subjected to said gas concentration and to convert detected gas pressure into an electrical signal;

an amplifier connected to amplify said electrical signal; and a differential amplifier having an invertible input connected to receive said amplified signal and a non-inverting input connected to receive said voltage and having its output connected to said indicating device for energization thereof, said differential amplifier means adapted to automatically adjust said voltage by an amount corresponding to variations in said voltage created by atmospheric pressure changes applied to said sensor and thereby provide said output with values compensated for changing atmospheric pressure such that said indicating device indicates true gas concentration unaffected by variations in atmospheric pressures.

2. A gas analysis sensor in accordance with claim 1, including a power supply connected in parallel with said pressure-sensitive module.

3. A gas analysis sensor in accordance with claim 1, including a potentiometer connected in series with said sensor for calibration.

* * * * *